United States Patent [19]

Szabo

[11] Patent Number: 4,647,221

[45] Date of Patent: Mar. 3, 1987

[54] METHOD OF AND APPARATUS FOR THE DETERMINATION OF THE THERMAL INSULATING PROPERTIES OF BUILDING WALLS

[75] Inventor: Paul Szabo, Ebikon, Switzerland

[73] Assignee: Digana Ag, Wallisellen, Switzerland

[21] Appl. No.: 800,130

[22] PCT Filed: Mar. 20, 1985

[86] PCT No.: PCT/CH85/00047

§ 371 Date: Nov. 1, 1985

§ 102(e) Date: Nov. 1, 1985

[87] PCT Pub. No.: WO85/04479

PCT Pub. Date: Oct. 10, 1985

[30] Foreign Application Priority Data

Mar. 23, 1984 [CH] Switzerland .................. 1475/84

[51] Int. Cl.⁴ .................. G01K 17/20; G01N 25/18
[52] U.S. Cl. .................. 374/44; 374/30
[58] Field of Search .................. 374/43, 44, 159

[56] References Cited

U.S. PATENT DOCUMENTS

| | | | |
|---|---|---|---|
| 3,045,473 | 7/1962 | Hager, Jr. | 374/44 |
| 3,075,377 | 1/1963 | Lang | 374/44 |
| 4,059,982 | 11/1977 | Bowman | 374/204 X |
| 4,095,454 | 1/1978 | Fisher | 374/43 |
| 4,236,403 | 12/1980 | Poppendiek | 374/44 |
| 4,246,785 | 1/1981 | Sellers et al. | 374/159 |

FOREIGN PATENT DOCUMENTS 0065433 11/1982 European Pat. Off. .
2939053 7/1980 Fed. Rep. of Germany .

OTHER PUBLICATIONS

"Transmission of Heat by Conduction and Connection" by W. H. McAdams, Mechanical Engineers Handbook 6th Edition, 1958, pp. 4-92 and 4-93.

Primary Examiner—Daniel M. Yasich
Attorney, Agent, or Firm—Karl F. Ross; Herbert Dubno

[57] ABSTRACT

The installation for determining the thermal resistance of a wall comprises a first measuring unit applicable to the inner side, respectively the warm side of the building element, the unit comprising a measuring plate made of heat conducting material having a given thermal resistance of which one face is intended to be applied to the building element and of which the other face is in thermal contact with an adjustable plane heating body. The measuring plate provides by means of thermocouples arranged on either face a reference signal corresponding to the heat flow through the measuring plate to an electronic control and calculating unit. Furthermore a second measuring unit arranged on the outer side or cold side of the building element comprises at least one contact plate made of heat conductor material covering the measured area and connected to the control and circulation unit by at least another thermocouple. Thereby, it is possible to provide a measuring plant which is easy to handle, practical and which enables obtaining high precision measurements which are negligibly influenced by boundary conditions.

9 Claims, 2 Drawing Figures

METHOD OF AND APPARATUS FOR THE DETERMINATION OF THE THERMAL INSULATING PROPERTIES OF BUILDING WALLS

CROSS REFERENCE TO RELATED APPLICATIONS

This application is a national phase application corresponding to PCT/CH85/00047 filed 20 Mar. 1985 and based in turn, upon a Swiss national application 1475/84-8 filed 23 Mar. 1984.

FIELD OF THE INVENTION

My present invention relates to a method of determining the thermal insulating properties of buildings, especially outer walls, by measuring the temperature drop between surfaces of the structure, particularly the inner surface and outer surface of the outer wall. The invention also relates to apparatus for this purpose.

BACKGROUND OF THE INVENTION

Increase in price and the foreseeable shortage of energy have drawn the problem of effective structural insulation against a loss of heat into the foreground. In these considerations, the dynamic heat transmission through the shell of the building is dominant; for this reason the thermal optimization of the shell of the building required as a central focus insulation against loss of heat, primarily by the reduction of heat transmission through the structural parts of the shell of the building by means of thermal insulation.

The areal thermal transmittance is characterized by the K-Value and mathematically determined according to present practice from the mathematical values of the thermal conductivity of the building materials. These values were, in turn, determined by numerous measurements. Note the article "Transmission of Heat By Conduction and Convection" by W. H. Adams in pages 92 and 93 of the Mechanical Engineers Handbook, Mc Graw Hill book Co., 6th Edition (1958).

The determination of the K-value can be an actual measurement from the thermal transmission of the structure. In construction engineering, one speaks, therefore, of the K-value measurement, which means precisely this thermal transmission measurement.

Since the K-value quantifies the thermal insulation capabilities of the structure, it can be defined by certain standards. The planner can follow these standard requirements accordingly. Inaccuracies in construction, alterations of the plans, utilization of building materials of different quality, uncoordinated working stretches etc. can, however, give rise to thermal insulation abilities (K-values) different from the original plan. The necessity for monitoring the heat transmission coefficient is therefore obvious.

The monitoring of the heat transmission of a building is particularly problematical because the measurement has to take place under non-steady state conditions, that is, under constantly changing temperatures and air currents as well as under changing thermal radiation conditions. The measuring of the K-value under these non-steady conditions takes place, then, by way of the heat flow measurement, whereby there are three prerequisites, namely: a constant heat flow direction over a long period a sufficient integration period in order to attain representative average values, and continual control of the measuring.

These three prerequisites lead to difficulties that make a routine execution of such measurments impossible because:

the known methods of measurement make measuring possible only in the cold season;

the natural mean temperature difference has to lie above 10 K.;

outside constructions bathed in sunshine connot be measured; and an almost steady room temperature is required and only very long measuring times permit the determination of representative results.

OBJECT OF THE INVENTION

It is therefore an object of the present invention to provide a method of measurement that can be generally and properly employed with the necessary accuracy of measurement, only slightly influenced by the boundary conditions.

Another object is to provide improved apparatus for this purpose.

SUMMARY OF THE INVENTION

This is achieved according to invention in that for generating a quasi steady or controlled non-steady condition in a measuring area, a temperature drop is forced thereupon so that, in comparison, the natural, non-steady state temperature drop can be disregarded.

In order to avoid imprecise measurement due to lateral heat transfer in the building, the measuring area is situated within a plane extension which is encircled by a boundary field, in which a temperature drop is likewise forced upon the building structure.

Due to these steps, a relatively wide field with identical thermal conditions is created, in the core of which, as in point-focal measurement, a vertical heat flow approximately parallel, to the surface of the wall vertical heat flow exists. With these steps, then, a thermal curtain, as it were, is laid around the field of measurement.

Furthermore, the present invention relates to apparatus for carrying out the method which comprises a first adjustable measuring unit on the inner side or warm side of the building, which comprises a measuring plate of heat-conducting material with given thermal insulating property, one side of which is for attaching onto the building, and the other side of which is in heat transfer contact a controllable laminar heater, with the measuring plate supplying a reference signal, by way of bilateral thermal elements, according to the thermal flow through the measuring plate to an electronic control and evaluation part of the apparatus. The latter also includes a second attachable measurement unit on the outer side or cold side of the building which comprises at least one contact plate of heat-conducting material, covering the measuring area, connected with the control and evaluation part by at least one further thermal element.

These steps permit the conception of a measuring equipment that is easy to handle and therefore in practice properly usable, and that guarantees, from boundary conditions only disregardably affected, high exactitudes of measurement. Remarkable thereby is a large-surface transfer of heat given off from the laminar heater over the measuring plate onto the building structure, so that at least in a middle area of the measuring field only a negligibly small lateral heat flow in the building can be expected.

To further reduce measurement imprecision due to lateral heat flow, it is, as previously mentioned, necessary to create a large field of measurement with identical thermal conditions in order to achieve in the center of this field a heat flow as parallel as possible, perpendicular to the surface of the wall.

This can be achieved according to invention first in that the laminar heater is made variably heatable in particular surface areas, whereby, naturally, the temperatures in the boundary regions have to be greater than in the center. This can be achieved, for example, by means of a heat mat with a spiral resistance heater, the coils of which are thicker or lie closer together in the boundary region.

An important improvement is achieved in particular when the measuring plate projects with a boundary field the shape of a frame over the laminar measuring area, with which boundary field a further heater, constructed the shape of a frame and thermally separated from the surrounding heater, is in heat-transfer contact.

For an optimal temperature taking at a sufficient temperature drop for gaining an evaluable comparison signal, as well as to optimize the thermal conductivity on the measuring plate, according to invention, the measuring plate has a metallic coating on both sides within its boundary field and which corresponds to the size of the measuring field on the building.

To be able, then, to preprogram controls such measurement equipment and make the measurement results immediately recognizable, it is advantageous when the measurement unit for the warm side comprises at least one detecting element, determining the temperature in the boundary region of the measuring field on the building, and which supplies a control signal for the temperature control on the frame-shaped heater, and when, furthermore, the lamina heater as well as the frame-shaped heater each supply a feed-back signal for a rheostat on the control and evaluation part by way of at least one thermal element.

A previously mentioned, the influences of the climatic fluctuations on the heat flow through an outer wall or the like is a problem. A perfect elimination of such fluctuations is of course out of the question. Apart from the fact that such a perfect screening off of the measuring region is not possible, a new method of measurement must be such that the expenditure is smaller rather than larger.

This screening is, therefore, should be such that the fluctuations for a short period of time do not reach the measuring area or affect it only weakly. Above all, the direct influence of radiation has to be avoided. Thereby, the equalization of temperature with the environment i.e. to the air temperature, has to be maintained. In this connection, it is to be avoided, however, that this protected air space becomes an additional insulation layer.

Such a screening off is attained according to invention in that the contact plate is surrounded on its outside by a thermal cover with a perforated heat exchange area. It is advantageous if the thermal cover comprises a perforated frame surface area extending over the inner surface area covering the contact plate, and, further, when a reflector coating is applied to the outside of the heat exchange areas of the thermal cover.

For an easy handling of the measurement equipment according to invention, it is, in addition, of considerable advantage when the measuring unit for the warm side is supported at its free end by an adjustable lever means of a support arrangement, and when the measuring unit for the cold side is attached at its free end to a hinged arm arrangement supported on a building.

SPECIFIC DESCRIPTION

Figure 1:
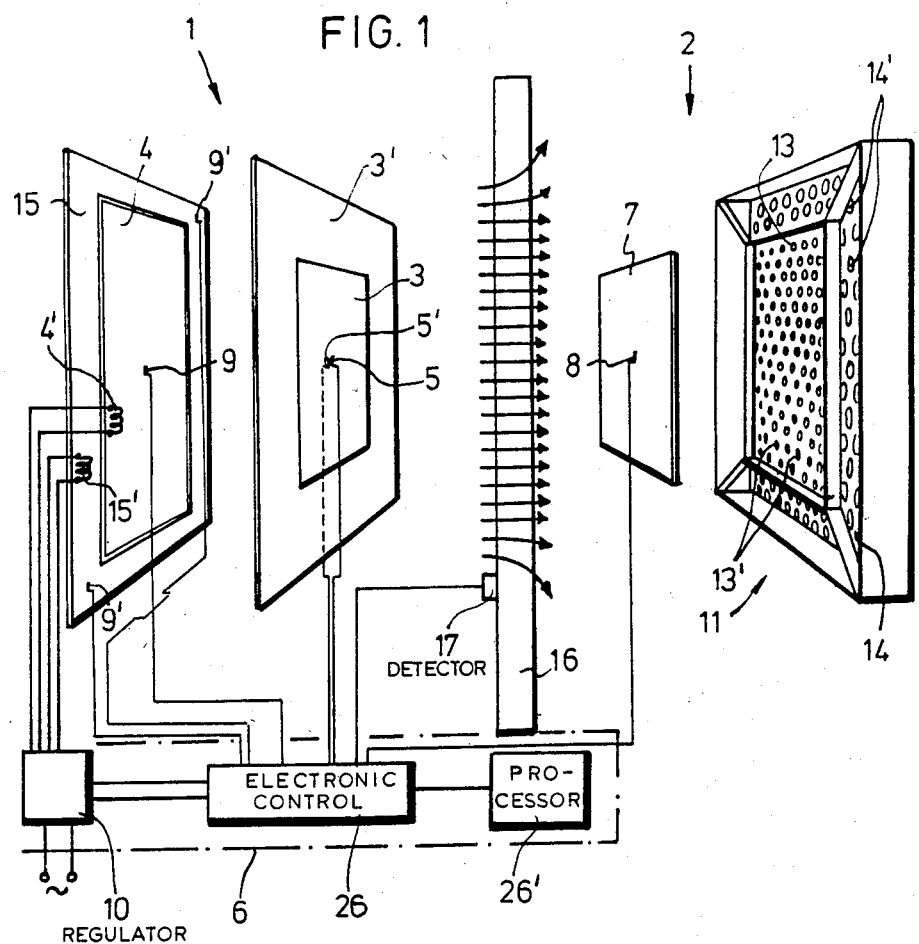
FIG. 1 is a basic diagram of the measuring equipment for the determination of the thermal insulating property of a building structure according to invention.

The measuring equipment for the determination of the thermal insulation propery of buildings, for example on the outer wall 16 of a building, as indicated in the drawing, is based on the method of measurement according to invention, whereby a temperature drop is forced upon the measuring area of the building to considerably eliminate the effect of boundary conditions which can distort the results of the measurement, as has been described in detail in the introduction.

For this, the measuring equipment comprises a first adjustable measuring unit 1 on the inner side or warm side of the building, which comprises, among other things, a measuring plate 3 of heat-conducting material with given thermal insulating property, one side of which is for attaching onto the building, and the other side of which is in heat-transfer contact with a controllable laminar heater 4. Here, the measuring plate 3 supplies a reference signal, by way of bilateral thermal elements 5 and 5', according to the thermal flow through the measuring plate to an electronic control and evaluation part 6 of the equipment.

Further, the measuring equipment comprises according to invention a second attachable measuring unit 2, on the outer side or cold side of the building, which comprises at least one contact plate 7 of heat-conducting material, covering the measuring area, connected with the control and evaluation part 6 by at least one further thermal element 8.

From FIG. 1 in particular, it can be further seen that the measuring plate 3 projects with a boundary field 3' the shape of a frame over the laminar measuring area, with which boundary field or frame 3' a further heater 15, constructed the shape of a frame and thermally separated from the surrounded heater 4, is in heat-transfer contact.

As previously illustrated by way of introduction, the laminar heater 4 should be heatable in particular surface areas, which is not shown here in detail. The heating elements 4' are thereby controlled from a regulator 10 which receives its regulating signal from a control electronic 26 of the control and evaluation part 6 which is coupled to a processor 26' which can comprise in the usual way a calculator, a monitor and a printer. Moreover, for an optimal temperature control, the measuring unit 1 for the warm side comprises at least one detecting element 17, determining the temperature in the boundary region of the measuring field on the building, and supplies a control signal for the temperature control of the frame-shaped heater 15. The respective heating elements 15' of the frame heater 15 are likewise controlled by a regulator 10. It is advantageous to provide thermal elements 9 or 9' on the laminar heater 4 or on the frame-shaped heater 15, which, for automatic regulation in particular, supply feed-back signals to the control electronic 26.

As previously mentioned, the measuring plate 3 supplies the necessary reference signal for the mathmatical determination of the K-value. For an optimization of the conditions, the measuring plate 3, which is preferably of PVC, has, therefore, a metallic coating on both sides within its boundary field 3' and which corresponds to the size of the measuring field on the building.

The size of these metal sheetings or coatings is chosen in such a way that they can cover the joints, still somewhat proportionally, even with large block-stone masonry. At a size of 0.6×0.6 m., two layer joints are covered for certain, and probably two butt joints. The butt joints play a lesser role, thereby, since they are filled as a rule with insulating material. The taking of the temperature of the sheetings can, as mentioned, take place with thermal elements which are brought into full contact with the metal. Since the distribution of temperature is guaranteed, two points of taking suffice (only one taking shown).

For the considerable elimination of change in the outer climates or the cold side of the building 16, a so-called thermal cover 11, as mentioned, provided, which covers over the outer contact plate 7 on its outer side. For an unrestricted air circulation, the heat exchange area 13 of the thermal cover 11 is, therefore, provided with perforations 13'. The thermal cover 11 is, thereby, so developed that this comprises a perforated frame surface area 14, extending over the inner surface area 13, covering the contact plate 7, which is likewise provided with perforations 14' Moreover, it is advantageous when a reflecting coating is added to the outside of the heat exchange area 13, 14 of the thermo cover 11.

Thus, from the foregoing there results a method of measurement as well as equipment according to invention for the determination of the thermal insulating property of buildings, esp. outer walls, which fulfill all presented requirements, whereby, of course, the underlying idea of the invention is not confined only to the aforementioned, any desired modifications are possible. In particular, with regard to size, choice of material, feeler means, and parts of the control and evaluation arrangement, there are no restrictions essential to the invention.

It stands to reason, therefore, that the elements of the measuring means 1 for the warm side, as well as also the element of the measuring unit 2 for the cold side, are integrated in appropriate manner into a compact, easy-to-handle, one-piece system.

In this connection, the affixation of both systems 1 and 2 can themselves be on the one or the other side of the wall, as may be desired.

Figure 2:
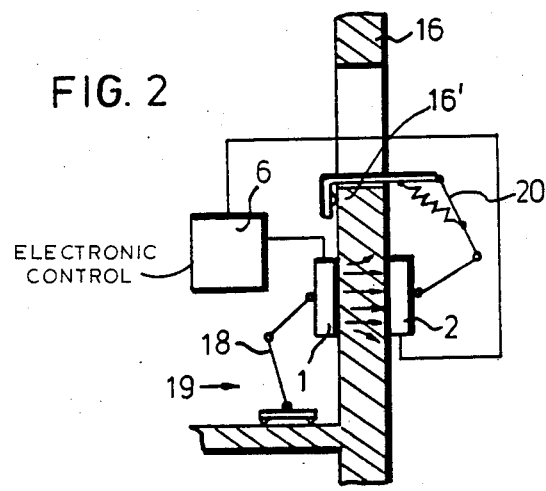
FIG. 2 is a side view and diagrammatic representation of an embodiment of the measuring equipment according to invention according to FIG. 1.

FIG. 2 shows a specific arrangement where the measuring unit 1 for the warm side is supported at its free end by the adjustable lever means 18 of a support arrangement 19, and where the measuring unit 2 for the cold side is attached at its free end to a hinged arm arrangement 20 supported on a building.

For this, the latter can, for example, grip behind a window-sill 16' of the building 16.

What is claimed is:

1. A method of determining the thermal transmissivity of a building wall, comprising the steps of:
   applying a measuring plate to a measuring area of an interior surface of said wall;
   inducing a thermal flow from said interior surface to an exterior surface of said wall by heating said plate with a laminar heater;
   measuring temperatures at said plate and at a further measuring plate applied to said exterior surface in registry as the measuring plate applied to said exterior surface and calculating from said temperatures the thermal transmissivity per unit area of the area of said wall between said plates; and
   eliminating extraneous influences upon the resulting measurement at least in part by heating said interior surface with a further laminar heater all around the periphery of the measuring plate in contact with said interior surface, the heat applied by said heaters being sufficient to render transient thermal effects by natural temperature gradients between said walls negligible.

2. The method defined in claim 1 wherein said measuring plate on said interior wall is surrounded by a thermally conductive frame registering with said additional heater and through which heat is transferred to said wall, further comprising the step of controlling said heaters in response to temperature measurements on said heaters.

3. The method defined in claim 2, further comprising the step of enclosing said measuring plate on said exterior surface of said wall in a shield permeable to ambient atmosphere but blocking direct impingement of solar energy on said measuring plate on said exterior surface.

4. An apparatus for determining the thermal transmissivity of a building wall, comprising:
   an interior thermally conductive measuring plate adapted to be applied to an interior surface of a building wall for an area thereof in which said transmissivity is to be measured;
   an exterior measuring plate applicable to an exterior surface of said wall registering with said interior measuring plate and juxtaposed therewith across said area of said wall;
   respective thermal elements on said measuring plates for detecting temperatures thereof and coupled with electronic circuitry for calculating said thermal transmissivity;
   a first laminar heater acting upon said interior measuring plate for heating an area of said wall through said interior measuring plate to a temperature sufficient to create a forced thermal gradient across said area of said wall; and
   a second laminar heater for heating said wall at said interior surface all around the periphery of said interior measuring plate to a temperature sufficient to render extraneous influences upon said gradient negligible in determining said thermal transmissivity.

5. The apparatus defined in claim 4 wherein said interior measuring plate is rectangular and is surrounded by a rectangular thermally conductive frame, said second laminar heater registering with said frame and heating said wall therethrough, both said heaters being provided with respective temperature measuring elements connected in a feedback circuit for control of the respective heater.

6. The apparatus defined in claim 5, further comprising another temperature sensitive element responsive to temperature of said interior surface around said frame for controlling at least said second heater.

7. The apparatus defined in claim 5, further comprising an air-permeable solar radiation shield covering said exterior measuring plate.

8. The apparatus defined in claim 7 wherein said shield is provided externally with reflective surfaces.

9. The apparatus defined in claim 5 wherein at least one of said measuring plates is mounted on an articulated arm arrangement for pressing it against the respective surface of said wall.

* * * * *